(12) United States Patent
Antons et al.

(10) Patent No.: US 6,310,254 B1
(45) Date of Patent: Oct. 30, 2001

(54) METHOD FOR PRODUCING OPTICALLY ACTIVE AMINO ALCOHOLS

(75) Inventors: Stefan Antons, Leverkusen (DE); Andreas Schulze Tilling, League City, TX (US); Erich Wolters, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,966

(22) PCT Filed: Jan. 16, 1999

(86) PCT No.: PCT/EP99/00233

§ 371 Date: Jul. 25, 2000

§ 102(e) Date: Jul. 25, 2000

(87) PCT Pub. No.: WO99/38838

PCT Pub. Date: Aug. 5, 1999

(30) Foreign Application Priority Data

Jan. 31, 1998 (DE) .............................................. 198 03 892

(51) Int. Cl.[7] ................................................... C07C 215/00
(52) U.S. Cl. ......................... 564/503; 568/885; 500/265; 564/355
(58) Field of Search .................................. 564/503, 355; 568/885; 500/265

(56) References Cited

U.S. PATENT DOCUMENTS

| | | | | |
|---|---|---|---|---|
| 4,990,655 | * | 2/1991 | Kitson et al. | 500/265 |
| 5,061,671 | * | 10/1991 | Kitson et al. | 502/185 |
| 5,478,952 | * | 12/1995 | Scwartz et al. | 594/325 |
| 5,536,879 | * | 7/1996 | Antons et al. | 564/503 |

* cited by examiner

Primary Examiner—Gary Geist
Assistant Examiner—Hector Reyes
(74) Attorney, Agent, or Firm—Joseph C. Gil; Richard E. L. Henderson

(57) ABSTRACT

The invention relates to a process for preparing optically active amino alcohols from optically active amino acids by reducing an optically active amino acid with hydrogen in the presence of a ruthenium-containing catalyst and an acid.

10 Claims, No Drawings

METHOD FOR PRODUCING OPTICALLY ACTIVE AMINO ALCOHOLS

The present invention relates to an improved process for preparing optically active amino alcohols by reduction of corresponding amino acids using ruthenium catalysts.

A process for preparing optically active amino alcohols by catalytic hydrogenation of the corresponding amino acids over ruthenium catalysts is described in EP-A 696 575. The enantiomeric excesses of the amino alcohols prepared in this way do not yet meet the high demands made of precursors for pharmaceuticals and crop protection agents. In addition, the achievable yields and the reaction times required in the process of EP-A 696 575 are not particularly favourable.

There is therefore a need for a process for preparing optically active amino alcohols having an enantiomeric excess of over 99% which can be carried out readily, simply and inexpensively.

We have now found a process for preparing optically active amino alcohols from optically active amino acids by reduction with hydrogen in the presence of ruthenium-containing catalysts, which is characterized in that the reduction is carried out with addition of acids.

The process of the invention can be carried out using, for example, optically active amino acids of the formula (I)

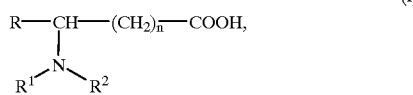

where
R represents straight-chain or branched $C_1$–$C_{12}$-alkyl, $C_7$–$C_{12}$-aralkyl or $C_6$–$C_{10}$-aryl, which may each be substituted by $NR^3R^4$, OH or COOH,
$R^1$, $R^2$, $R^3$ and $R^4$ each represent, independently of one another, hydrogen, straight-chain or branched $C_1$–$C_{12}$-alkyl or $C_3$–$C_8$-cycloalkyl, where
$R^1$ and $R^2$ and also $R^3$ and $R^4$ may in each case, independently of one another, together also represent —$(CH_2)_m$—, where m=an integer from 4 to 7, and where R and $R^1$ may together also represent —$(CH_2)_o$—, where o=an integer from 2 to 6, and
n represents zero or an integer from 1 to 5,
to give optically active amino alcohols of the formula (II)

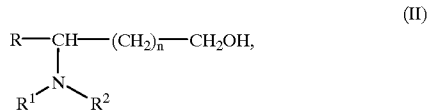

where
R, $R^1$, $R^2$ and n are as defined for formula (I).

In the formulae (I) and (II), R preferably represents straight-chain or branched $C_1$–$C_4$-alkyl which may be substituted by $NR^3R^4$, OH or COOH or represents benzyl. $R^1$, $R^2$, $R^3$ and $R^4$ preferably each represent, independently of one another, hydrogen or straight-chain or branched $C_1$–$C_4$-alkyl, where $R^1$ and $R^2$ and also $R^3$ and $R^4$ may in each case, independently of one another, together also represent —$(CH_2)_m$—, where m=4 or 5, and where R and $R^1$ may together also represent —$(CH_2)_o$—, where o=3 or 4. n preferably represents 0, 1 or 2.

In addition, preference is given to $R^1$ and $R^2$ being identical or together representing a polymethylene bridge. The same applies to $R^3$ and $R^4$.

Particularly preferred amino acids of the formula (I) are alanine, valine, leucine, isoleucine, threonine, ornithine, aspartic acid, glutamic acid, phenylalanine and proline.

The process of the invention can be carried out, for example, with addition of from 0.5 to 1.5 equivalents of an organic or inorganic acid per 1 equivalent of basic groups in the optically active amino acid used. As acids, preference is given to inorganic acids, in particular sulphuric acid, hydrochloric acid and phosphoric acid. The acids can, for example, be used as such, in the form of aqueous solutions or in the form of their separately prepared adducts with the amino acids used, e.g. as sulphates, hydrogensulphates, hydrochlorides, phosphates, dihydrogenphosphates or monohydrogenphosphates.

The amount of acid to be added is preferably selected so that after its addition all carboxyl groups in the amino acid used are present in protonated form. Preference is given to using from 1 to 1.3 equivalents of organic or inorganic acid per equivalent of basic groups of the amino acids.

Suitable catalysts for the process of the invention are, for example, ruthenium, bimetallic ruthenium/metal X catalysts and trimetallic ruthenium/metal X/metal Y catalysts, which can all be used as such or applied to a support material. The metals X and Y can each be, for example, a metal selected from the group consisting of metals and transition metals having atomic numbers in the range from 23 to 82. The catalysts can contain ruthenium and, if desired, the metals X and, if desired, the metals Y in various forms, for example in elemental form, in the form of compounds of ruthenium or of ruthenium and the metals X or of ruthenium and the metals X and Y or in the form of an intermetallic compound of ruthenium and the metal X and, if desired, the metal Y. If the catalysts are not used in supported form, they can be present, for example, in colloidal form or as finely divided solid. Examples of catalysts are finely divided ruthenium/rhenium, ruthenium/osmium, ruthenium/iron, ruthenium/cobalt, ruthenium/rhodium, ruthenium/palladium, ruthenium/platinum, ruthenium/copper, ruthenium/zinc, ruthenium/silver, ruthenium/tin, ruthenium/germanium, ruthenium/gallium, ruthenium/lead, ruthenium/rhenium/copper, ruthenium/rhenium/silver and ruthenium/rhenium/tin particles, for example in metallic form or in the form of their oxides, hydroxides, halides, nitrates, carboxylates, acetylacetonates or as amine complexes.

Suitable support materials are, for example, carbons, carbon blacks, graphites, aluminium oxides, silicon dioxides, silicates, zeolites and clays. Supported catalysts may contain, for example, from 1 to 50% by weight of metal in elemental form or in the form of compounds.

The catalysts to be used may, if desired, have been modified by treatment with sulphur compounds, e.g. thioethers.

Preference is given to catalysts which contain ruthenium and rhenium without a support and as bimetallic catalyst particles have a high specific surface area, e.g. from 50 to 150 $m^2$/g. Such catalysts can be prepared, for example, by reductively precipitating rhenium from a rhenium solution onto a ruthenium oxide hydrate having a high surface area (e.g. from 50 to 300 $m^2$/g) by action of hydrogen. This gives a bimetallic catalyst having a high surface area and intimate contact between the two metals. Surprisingly, the reduction of the dissolved rhenium can be carried out in the presence of ruthenium at significantly lower temperatures than in the absence of ruthenium. In principle, the deposition of a second metal can be carried out as part of the catalyst preparation or in situ in the hydrogenation reaction.

Based on 1 mol of optically active amino acid used, the amount of catalyst employed can be, for example, from 0.1 to 10 g of metal or metal compounds or from 1 to 50 g of supported catalysts containing metal or metal compounds.

The process of the invention is generally carried out in the presence of a solvent for the optically active amino acids and optically active amino alcohols. Suitable solvents are, for example, water, water-miscible organic solvents and mixtures of the two. As water-miscible solvents, mention may be made of lower alcohols and water-miscible ethers. Preferred solvents are water and mixtures containing water and lower alcohols or tetrahydrofuran.

The process of the invention can be carried out, for example, at temperatures in the range from 0 to 150° C. and pressures in the range from 5 to 300 bar. Preference is given to temperatures of from 0 to 130° C. and pressures of from 10 to 280 bar. Particular preference is given to temperatures of from 30 to 80° C. and pressures of from 150 to 250 bar. It is also possible, if desired, to commence the reduction with hydrogen at a relatively low pressure, e.g. at from 50 to 150 bar, and then to complete it at relatively high pressures, e.g. from 150 to 300 bar. The reaction is complete when no more hydrogen is taken up, which is generally the case after from 1 to 10 hours. At low pressures and low temperatures, the reaction time can also be longer.

To work up the reaction mixture, it is possible, for example, firstly to cool the reaction mixture, to separate off the catalyst, e.g. by filtration, to remove the volatile constituents present (generally solvents and water of reaction) partially or completely by distillation, if desired under reduced pressure, to liberate the amino alcohol from its salt in the residue by means of base (e.g. aqueous alkali metal hydroxide or alcoholic alkoxide solution), to separate off the precipitated salt and to fractionate the filtrate under reduced pressure. The catalyst which has been separated off can be re-used, likewise the solvent.

The process of the invention can be carried out continuously, semicontinuously or batchwise. Suitable reactors are, for example, stirred vessels and trickle phase reactors. The process is advantageously carried out as a batch feed stream process, with the catalyst being initially charged in the solvent and the acid solution of the amino acid being pumped in at the rate at which it is consumed in the hydrogenation. This enables the concentration of the amino acid salt in the reactor to be kept at a low level, which has a positive effect on the catalyst life and the yield and lowers the corrosiveness of the reaction medium.

The process of the invention has the advantages that in the hydrogenation of optically active amino acids using a ruthenium-containing catalyst, optically active amino alcohols are obtainable in higher purity, with a higher enantiomeric excess, in higher yield, at lower temperatures and in shorter reaction times than is possible without addition of acid. It has also been found that a catalyst containing at least one further metal, in particular rhenium, in addition to ruthenium has significantly better performance in the hydrogenation of optically active amino acids than a monometallic ruthenium catalyst. These advantages of this process are extraordinarily surprising.

EXAMPLES

Unless otherwise indicated, percentages are by weight.

Example 1

In a 0.71 stainless steel autoclave, 3.9 g of rhenium(VII) oxide (76.87% Re) were added to a suspension of 33.6 g of moist (with water) ruthenium oxide hydrate (8.93% Ru) having a surface area of 210 m$^2$/g in 100 ml of water. After flushing with nitrogen, 100 bar of hydrogen were injected and the mixture was heated to 120° C. The hydrogen pressure was then increased to 150 bar and the mixture was stirred for 1 hour at 120° C.

A solution of 60.0 g of L-alanine and 32.9 g of sulphuric acid in 370 g of water was added to the resulting suspension of Ru-Re black. After flushing with nitrogen, the autoclave was closed and 100 bar of hydrogen were injected. Over a period of 30 minutes, the temperature was increased to 60° C. and the hydrogen pressure was increased to 200 bar. After a reaction time of 7 hours, hydrogen absorption had ceased. The autoclave was cooled to room temperature, vented, the catalyst was separated from the reaction mixture by filtration and the water was distilled from the filtrate. The residue was brought to a pH of 11.4 using 59.7 g of 45% strength aqueous sodium hydroxide and fractionally distilled at 50 mbar. This gave 35.7 g of pure L-alaninol (bp.: 94° C./50 mbar), ee>99.9%. This corresponds to a yield of 71% of theory. Here and in the other examples, the ee was determined by gas chromatography.

Example 2

The procedure of Example 1 was repeated, but the hydrogenation was carried out at 80° C. Hydrogen absorption was complete after 5 hours. 35.0 g of pure L-alaninol were obtained, corresponding to a yield of 69% of theory. The ee was >99.9%.

Example 3

The procedure of Example 1 was repeated, but the hydrogenation was carried out at 100° C. Hydrogen absorption was complete after 3 hours. 26.5 g of pure L-alaninol were obtained, corresponding to a yield of 53% of theory. The ee was 90.3%.

Example 4

Example 1 was repeated 5 times, with each repetition being carried out using the catalyst separated off from the previous batch. No change in the enantiomeric excess of the resulting L-alaninol was found.

Example 5

The procedure of Example 1 was repeated, but the equivalent molar amount of L-valine was used in place of L-alanine. Distillation gave 33.5 g of pure L-valaninol. This corresponds to a yield of 49% of theory. The ee was above 99.9%.

Example 6

The procedure of Example 1 was repeated, but no rhenium(VI) oxide was added in the catalyst preparation. The hydrogenation time was 35 hours. The work-up gave 36.2 g of pure L-alaninol, corresponding to a yield of 72% of theory. The ee was above 99.9%.

Example 7 (comparative example)

The procedure of Example 2 was repeated, but no sulphuric acid was added and no aqueous sodium hydroxide was added after the catalyst had been separated off. After 20 hours, no more hydrogen was taken up. The work-up gave 7.3 g of pure L-alaninol, corresponding to a yield of 15% of theory. The ee was 94.2%.

Example 8

58.8 g of moist (with water) RuO$_2$ (10.19% Ru), 7.8 g of Re$_2$O$_7$ (76.9% Re) and 100 ml of water were placed in a 0.71 stainless steel autoclave. After flushing with nitrogen, 100 bar of H$_2$ were ejected and the mixture was heated to 120° C. while stirring (800 rpm). After reaching this temperature, the H$_2$ pressure was increased to 150 bar and the catalyst was prereduced at 120° C. for one hour.

After cooling the autoclave to 70° C., a solution of 138 g of L-alanine (99.2% pure) (1.54 mol) in 256 g of 30% strength aqueous $H_2SO_4$ was added to the resulting suspension of Ru-Re black and the $H_2$ pressure was increased to 200 bar. After 8 hours, hydrogen absorption had ceased.

After cooling to room temperature, the catalyst was filtered off from the reaction mixture and washed with 23 g of water.

This gave 548.4 g of crude solution from which 300 g of water were distilled on a rotary evaporator at 70° C. and 250–30 mbar.

279 g of 30% strength methanolic sodium methoxide solution were added dropwise to the residue over a period of 30 minutes while stirring at room temperature. The temperature rose to about 35° C. during the addition. The resulting suspension was stirred for another 15 minutes.

The precipitated sodium sulphate (116.3 g moist) was filtered off with suction and washed three times with 30 g each time of methanol. The residue was distilled via a 30 cm Vigreux column.

After a first fraction made up of 370 g of methanol/water, 94 g of (S)-2-amino-propanol (>99% pure according to GC) were obtained at 93–96° C. and 50 mbar.

This corresponds to a yield of 80% of theory.

The ee was 99.9%.

Examples 9–18

The amino acids shown in Table 1 were hydrogenated in the same way as in Example 8 (reaction conditions not optimized).

TABLE

| Example | Starting material | Product | Boiling point | Yield | ee |
|---|---|---|---|---|---|
| 9 | L-valine | L-valinol | 109° C./50 mbar | 72% | >99.9% |
| 10 | L-leucine | L-leucinol | 56° C./1 mbar | 48% | >99.9% |
| 11 | L-isoleucine | L-isoleucinol | 63° C./1 mbar | 56% | >99.9% |
| 12 | L-tert-leucine | L-tert-leucinol | 67° C./2 mbar | 31% | >99.9% |
| 13 | L-threonine | L-threoninol | 111° C./0.4 mbar | 61% | 98.7% |
| 14 | L-aspartic acid | L-aspartinol | 130° C./0.5 mbar | 60% | 98.9% |
| 15 | L-glutamic acid | L-glutaminol | 145° C./0.2 mbar | 58% | 98.3% |
| 16 | L-proline | L-prolinol | 53° C./0.4 mbar | 45% | 99.2% |
| 17 | L-pyroglutamic acid | L-pyroglutaminol | 168° C./0.4 mbar | 65% | 98.3% |
| 18 | L-phenylanine | L-cyclohexylalanine | 110° C./1 mbar | 32% | 99.3% |

What is claimed is:

1. A process for preparing optically active amino alcohols from optically active amino acids comprising reducing an optically active amino acid with hydrogen in the presence of a ruthenium-containing catalyst and an organic or inorganic acid other than said optically active amino acid.

2. A process according to claim 1 wherein
(i) the optically active amino acid has formula (I)

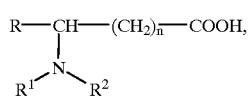

(I)

wherein

R represents straight-chain or branched $C_1$–$C_{12}$-alkyl, $C_7$–$C_{12}$-aralkyl or $C_6$–$C_{10}$-aryl, each of which may be substituted by $NR^3R^4$, OH, or COOH, $R^1$, $R^2$, $R^3$, and $R^4$ represent, independently of one another, hydrogen, straight-chain or branched $C_1$–$C_{12}$-alkyl, or $C_3$–$C_8$-cycloalkyl; $R^1$ and $R^2$ together and/or $R^3$ and $R^4$ together can, independently of one another, optionally represent —$(CH_2)_m$—, where m is an integer from 4 to 7; and R and $R^1$ together can optionally represent —$(CH_2)_o$—, where o is an integer from 2 to 6, and n represents zero or an integer from 1 to 5, and (ii) the resultant optically active amino alcohol has the formula (II)

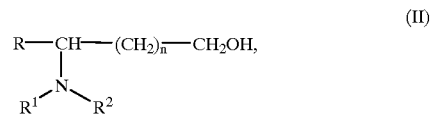

(II)

wherein R, $R^1$, $R^2$ and n are as defined for formula (I).

3. A process according to claim 1 wherein from 0.5 to 1.5 equivalents of the organic or inorganic acid are used per 1 equivalent of basic groups in the optically active amino acid.

4. A process according to claim 1 wherein the acid is sulphuric acid, hydrochloric acid, or phosphoric acid.

5. A process according to claim 1 wherein the optically active amino acid of the formula (I) is alanine, valine, leucine, isoleucine, threonine, ornithine, aspartic acid, phenylalanine, or proline.

6. A process according to claim 1 wherein the catalyst is ruthenium, a bimetallic ruthenium/metal X catalyst, or a trimetallic ruthenium/metal X/metal Y catalyst used as such or applied to a support, wherein X and Y independently represent a metal having an atomic number in the range of from 23 to 82.

7. A process according to claim 1 wherein the catalyst is used in metallic form or in the form of an oxide, hydroxide, halide, nitrate, carboxylate, acetylacetonate, or amine complex.

8. A process according to claim 1 wherein the catalyst contains ruthenium and rhenium without a support.

9. A process according to claim 1 carried out in the presence of water, a water-miscible organic solvent, or a mixture thereof.

10. A process according to claim 1 wherein the temperature of the reduction is in the range of from 0 to 150° C. and the pressure of the reduction is in the range of from 5 to 300 bar.

* * * * *